United States Patent [19]

Shaw et al.

[11] 4,138,366
[45] Feb. 6, 1979

[54] PROCESS FOR PRODUCING UNSATURATED ALIPHATIC ACIDS AND CATALYSTS THEREFORE

[75] Inventors: Wilfrid G. Shaw, Lyndhurst; David B. Terrill, Bedford, both of Ohio

[73] Assignee: The Standard Oil Company, Cleveland, Ohio

[21] Appl. No.: 742,489

[22] Filed: Nov. 17, 1976

Related U.S. Application Data

[63] Continuation-in-part of Ser. No. 683,367, May 5, 1976.

[51] Int. Cl.$^2$ .................... B01J 23/16; B01J 27/14; B01J 23/84
[52] U.S. Cl. .................... 252/464; 252/435; 252/437; 252/465; 252/467; 252/468; 252/469; 252/470
[58] Field of Search ............ 252/437, 468, 464, 467, 252/435, 465, 470, 469; 260/530 N

[56] References Cited

U.S. PATENT DOCUMENTS

| 3,684,741 | 8/1972 | Friedrichsen et al. | 252/437 X |
|---|---|---|---|
| 3,773,692 | 11/1973 | Hensel et al. | 252/467 X |
| 3,867,438 | 2/1975 | Hensel et al. | 260/530 N |
| 3,875,220 | 4/1975 | White et al. | 252/432 X |
| 3,954,855 | 5/1976 | Wada et al. | 260/530 N |
| 3,956,182 | 5/1976 | Ishimi | 260/530 N X |
| 3,965,163 | 6/1976 | Oda et al. | 252/435 X |
| 3,966,802 | 6/1976 | Takenaka et al. | 252/467 X |
| 3,997,600 | 12/1976 | Ferlazzo et al. | 260/530 N |
| 4,035,418 | 7/1977 | Okada et al. | 252/468 X |
| 4,042,625 | 8/1977 | Matsuzawa et al. | 252/435 X |
| 4,051,179 | 9/1977 | Sonobe et al. | 260/530 N |

*Primary Examiner*—Delbert E. Gantz
*Assistant Examiner*—William G. Wright
*Attorney, Agent, or Firm*—Herbert D. Knudsen; David J. Untener

[57] ABSTRACT

The present invention relates to a process for the production of unsaturated aliphatic acids and the catalyst therefore by the vapor phase oxidation of the corresponding unsaturated aliphatic aldehydes with molecular oxygen, optionally in the presence of steam, in the presence of an oxidation catalyst consisting of the oxides of the elements molybdenum, antimony and vanadium in combination with at least one of the oxides of the element selected from the group consisting of silver, magnesium, thallium and cadmium, and optionally one or more of the oxides of the elements of the group, manganese, cobalt, nickel, copper, iron, tin, chromium, titanium, bismuth, arsenic, phosphorus, rhenium, and zinc.

14 Claims, No Drawings

PROCESS FOR PRODUCING UNSATURATED ALIPHATIC ACIDS AND CATALYSTS THEREFORE

CROSS REFERENCE TO RELATED APPLICATION

This application is a continuation-in-part of our copending application Ser. No. 683,367 filed May 5, 1976.

BACKGROUND OF THE INVENTION

Catalyst compositions similar to those of the present invention are known for the oxidation of acrolein to acrylic acid. These include U.S. Pat. No. 3,725,472 which discloses the catalytic composition of molybdenum, vanadium and antimony; British Pat. No. 1,106,648 which claims a catalyst containing molybdenum, vanadium and antimony plus one of the elements of tin, nickel, chromium, and titanium; Belgium Pat. No. 763,243 which claims the combination molybdenum, vanadium, antimony plus tungsten; Belgium Pat. No. 773,851 which claims compositions containing in addition to the elements of molybdenum, vanadium, antimony and tungsten, the elements of lead, copper, tin, titanium and bismuth.

THE INVENTION

The present invention relates to an improved process for producing olefinically unsaturated carboxylic acids from the corresponding unsaturated aldehydes and to the catalyst composition employed therefore. More specifically, the present invention relates to a vapor phase process for producing acrylic acid or methacrylic acid from acrolein and methacrolein, respectively, by oxidation of the unsaturated aldehydes with molecular oxygen, optionally in the presence of steam, and in the presence of an oxidation catalyst having the empirical formula:

$$Mo_a Sb_b V_c Y_d Z_e O_f$$

wherein
Y can be one or more of the elements selected from the group consisting of silver, magnesium, thallium, and cadmium; and
Z can be one or more of the elements of the group consisting of manganese, cobalt, nickel, copper, iron, tin, chromium, titanium, bismuth, arsenic, phosphorus, rhenium, and zinc; and
wherein the number of atoms of each element present is represented by $a$ through $f$,
wherein
$a$ is a number from 6 to 18
$b$ is a number from 0.1 to 6
$c$ is a number from 0.1 to 6;
$d$ is a number from 0.01 to 6;
$e$ is a number from 0 to 6; and
$f$ is a number that satisfies the valence requirements of the other elements present.

Preferred are catalysts wherein $a$ is a number from 9 to 15; $b$ is a number from 0.7 to 3; $c$ is a number from 0.5 to 5; $d$ is a number from 0.05 to 1; and $e$ is a number from 0.0 to 1.

The elements in these catalysts are present in the form of their oxides or oxide complexes. In addition to the active catalytic ingredients, the catalysts of the invention may contain a support material. Suitable support materials include silica, alumina, zirconia, titania, silicon carbide, boron phosphate and the like. Preferred support materials are silica and alundum.

These catalysts are especially effective for preparing acrylic acid from acrolein and the preparation of methacrylic acid from methacrolein. The catalysts are also highly effective for oxidation reactions such as the oxidation of butadiene to maleic anhydride and the oxidative esterification of unsaturated aldehydes to the corresponding unsaturated ester. Preferred among these reactions is the production of unsaturated acids from the corresponding unsaturated aldehyde.

The oxidation of unsaturated aldehydes to obtain the corresponding acid is well known in the art. Basically, the invention, with respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely, with molar ratios of molecular oxygen to aldehyde of about 0.5 to about 5 normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam are added to the reactant feed per mole of aldehyde employed.

The reaction may be conducted in a fixed-bed or fluid-bed reactor, or forms thereof, using atmospheric, superatmospheric or subatmospheric pressure. The apparent contact time may vary considerably with contact times of a fraction of a second to 20 seconds or more normally being employed.

Using the catalyst of the invention, very desirable yields of unsaturated acid are obtained at low temperatures with the production of little or no acetic acid.

As noted above, catalysts very similar to the catalysts of the invention are known, see for example U.S. Pat. No. 3,567,773 and thus catalysts of this general type can readily be prepared by persons of ordinary skill in the art. Thus, the broad description of the invention makes the catalysts of the invention available.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 200° and 600° C. This calcination can take place outside of the catalytic reactor or an in situ activation can be utilized.

There are a number of preparations that could be used to make desirable catalysts of the invention. The preparation of catalysts of the invention used in the examples is shown in the Specific Embodiments.

SPECIFIC EMBODIMENTS

CATALYST PREPARATION

The catalysts of Comparative Example A and Examples 1-9 were prepared according to the following procedure:

EXAMPLE A

Catalyst $Mo_{12}Sb_1V_3O_{45.0}$

To 250 cc of hot distilled water was added 6.54 g of ammonium metavanadate. After approximately 15 minutes of heating and stirring, the reagent was dissolved and 39.50 g of ammonium heptamolybdate was added to the solution and dissolved. Then 2.71 g of antimony oxide ($Sb_2O_3$) was added. The solution was evaporated to near dryness with continual heating and stirring, and the contents were then placed in a drying oven at 110°-120° C. for 16 hours. The dried material was crushed and ground through a 50 mesh screen. A sufficient amount of powder was employed to coat 3/16" alundum spheres to achieve a 20 weight percent coating on the spheres. The coated spheres were then dried at 110°-120° C. for 3 hours and then activated by heat treating at 370° C. for 2 hours.

EXAMPLE 1

Catalyst $Mo_{12}Sb_1V_3Ag_{0.5}O_{45.5}$

The procedure of Comparative Example A was repeated using 6.37 g of ammonium metavanadate, 38.45 g of ammonium heptamolybdate and 1.51 g of silver acetate, followed by the addition of 2.64 g of antimony oxide ($Sb_2O_3$).

EXAMPLE 2

Catalyst $Mo_{12}Sb_1V_3Mg_{0.5}O_{45.5}$

The procedure of Comparative Example A was repeated using 6.48 g of ammonium metavanadate, 39.13 g of ammonium heptamolybdate and 1.98 g of magnesium acetate, followed by the addition of 2.64 g of antimony oxide.

EXAMPLE 3

Catalyst $Mo_{12}Sb_1V_3Tl_{0.2}O_{45.3}$

The procedure of Comparative Example A was repeated using 4.80 g of ammonium metavanadate, 29.0 g of ammonium heptamolybdate and 1.04 g of thallium acetate, followed by the addition of 2.02 g of antimony oxide.

EXAMPLE 4

Catalyst $Mo_{12}Sb_1V_3Cd_{0.2}O_{45.2}$

The procedure of Comparative Example A was repeated using 4.85 g of ammonium metavandate, 29.27 g of ammonium heptamolybdate and 0.736 g of cadmium acetate, followed by the addition of 2.01 g of antimony oxide.

EXAMPLE 5

Catalyst $Mo_{12}V_1Sb_1Mg_{0.2}O_{40.2}$

The procedure of Comparative Example A was repeated using 1.78 g of ammonium metavandate, 32.23 g of ammonium heptamolybdate and 0.65 g of magnesium acetate, followed by the addition of 2.21 g of antimony oxide.

EXAMPLE 6

Catalyst $Mo_{12}V_3Sb_1Ag_{0.5}Mn_{0.2}O_{45.5}$

The procedure of Comparative Example A was repeated using 4.75 g of ammonium metavanadate, 28.65 g of ammonium heptamolybdate, 1.13 g of silver acetate and 0.66 g of manganese acetate, followed by the addition of 1.97 g of antimony oxide.

EXAMPLE 7

Catalyst $Mo_{12}V_3Sb_1Cd_{0.2}Co_{0.1}O_{46.2}$

The procedure of Comparative Example A was repeated using 4.79 g of ammonium metavanadate, 28.95 g of ammonium heptamolybdate, 0.73 g of cadmium acetate and 0.34 g of cobalt acetate, followed by the addition of 1.99 g of antimony oxide.

EXAMPLE 8

Catalyst $Mo_{12}V_3Sb_1Cd_{0.2}P_{0.1}O_{46.4}$

The procedure of Comparative Example A was repeated using 4.79 g of ammonium metavanadate, 28.95 g of ammonium heptamolybdate, 0.73 g of cadmium acetate and 0.16 g of 85% phosphoric acid, followed by the addition of 1.99 g of antimony oxide.

EXAMPLE 9

Catalyst $Mo_{12}V_3Sb_1Tl_{0.2}Ni_{0.1}O_{46.6}$

The procedure of Comparative Example A was repeated using 4.75 g of ammonium metavanadate, 28.66 g of ammonium heptamolybdate, 1.03 g of thallium acetate, and 0.39 g of nickel nitrate hexahydrate, followed by the addition of 1.97 g of antimony oxide.

The catalysts prepared above were placed in a reactor constructed of 1.0 cm. inside diameter stainless steel tubing having a reaction zone of 20 c.c. The reactor was heated in a split block furnace. The reactor feed was a mixture of acrolein/air/$N_2$/steam in the molar ratio of 1/8.5/2.5/6. The reaction was conducted at atmospheric pressure, and the apparent contact time was 2 seconds. The reaction temperatures employed and the conversions obtained are summarized in Table I wherein the conversions reported are in terms of the following definitions:

$$\text{Percent Conversion} = \frac{\text{Moles of acrolein reacted} \times 100}{\text{Moles of acrolein fed}}$$

$$\text{Percent Single Pass Yield} = \frac{\text{Moles of product recovered} \times 100}{\text{Moles of acrolein fed}}$$

$$\text{Percent Selectivity} = \frac{\text{Moles of acrylic acid recovered} \times 100}{\text{Moles of acrolein reacted}}$$

The improved conversions of acrolein to acrylic acid obtained with the catalyst compositions of the present invention are readily apparent by the direct comparison of Examples 1-9 with Comparative Example A which represents a catalyst composition of the prior art.

In the same manner as shown by the examples above, other catalysts of the invention containing different amounts of silver, cadmium, magnesium and thallium and different optional elements such as manganese, nickel, tin, chromium, titanium, bismuth and the like, are used to produce acrylic acid.

Also using the catalysts of the invention, maleic anhydride, methacrylic acid or acrylates are made by known oxidation reactions.

TABLE I

Oxidation of Acrolein to Acrylic Acid

| Example No. | Catalyst Composition[1] | Reaction Temp., °C | % Conv. of Acrolein | [Corrected[2] % Single Pass Yield of] Acrylic Acid | Acetic Acid | % Selec. to Acrylic Acid |
|---|---|---|---|---|---|---|
| Comp. A | $Mo_{12}V_3Sb_1O_{45.0}$ | 332 | 43.8 | 34.8 | 0.7 | 79.5 |
| Comp. A | $Mo_{12}V_3Sb_1O_{45.0}$ | 356 | 66.1 | 49.2 | 1.4 | 74.4 |
| 1 | $Mo_{12}V_3Sb_1Ag_{0.5}O_{45.5}$ | 360 | 92.5 | 73.9 | 2.1 | 79.9 |
| 2 | $Mo_{12}V_3Sb_1Mg_{0.5}O_{45.5}$ | 338 | 99.2 | 93.0 | 1.5 | 93.8 |
| 3 | $Mo_{12}V_3Sb_1Tl_{0.2}O_{45.3}$ | 343 | 96.0 | 82.5 | 2.1 | 85.9 |
| 4 | $Mo_{12}V_3Sb_1Cd_{0.2}O_{45.2}$ | 349 | 85.8 | 76.1 | 1.1 | 91.0 |
| 5 | $Mo_{12}V_1Sb_1Mg_{0.2}O_{40.2}$ | 347 | 100.0 | 94.5 | 1.6 | 94.5 |
| 6 | $Mo_{12}V_3Sb_1Ag_{0.5}Mn_{0.2}O_{45.5}$ | 354 | 98.0 | 89.6 | 1.6 | 91.4 |
| 7 | $Mo_{12}V_3Sb_1Cd_{0.2}Co_{0.1}O_{46.2}$ | 331 | 99.2 | 92.9 | 1.5 | 93.6 |
| 8 | $Mo_{12}V_3Sb_1Cd_{0.2}P_{0.1}O_{46.4}$ | 349 | 99.2 | 90.2 | 2.2 | 90.9 |
| 9 | $Mo_{12}V_3Sb_1Tl_{0.2}Ni_{0.1}O_{46.6}$ | 368 | 97.5 | 84.4 | 2.8 | 86.6 |

[1]20% Active Catalyst Component Coated on 3/16" Alundum Sphere
[2]Corrected to 100% Carbon Balance.

We claim:

1. A catalyst having the empirical formula:

$$Mo_aSb_bV_cY_dZ_eO_f$$

wherein
Y can be one or more of the elements selected from the group consisting of silver, magnesium, thallium and cadmium; and
Z can be one or more of the elements of the group consisting of manganese, cobalt, nickel, copper, iron, tin, chromium, titanium, bismuth, arsenic, phosphorus, rhenium, and zinc; and
wherein the number of atoms of each element present is represented by $a$ through $f$,
wherein
$a$ is a number from 6 to 18
$b$ is a number from 0.1 to 6;
$c$ is a number from 0.1 to 6;
$d$ is a number from 0.01 to 6;
$e$ is a number from 0 to 6; and
$f$ is a number that satisfies the valence requirements of the other elements present.

2. The catalyst composition of claim 1 wherein $e$ is zero.

3. The catalyst of claim 1 wherein $a$ = 9 to 15; $b$ = 0.7 to 3; $c$ = 0.5 to 5; $d$ = 0.05 to 1; $e$ = 0.0 to 1; and $f$ is a number that satisfies the valence requirements of the other elements present.

4. The catalyst in claim 1 wherein Y is silver.
5. The catalyst in claim 1 wherein Y is magnesium.
6. The catalyst in claim 1 wherein Y is thallium.
7. The catalyst in claim 1 wherein Y is cadmium.
8. The catalyst in claim 1 wherein Y is selected from the group consisting of magnesium, thallium and cadmium.

9. The catalyst in claim 8 wherein $e$ is zero.
10. The catalyst in claim 8 wherein $a$ = 9 to 15; $b$ = 0.7 to 3; $c$ = 0.5 to 5; $d$ = 0.05 to 1; $e$ = 0.0 to 1; and $f$ is a number that satisfies the valence requirements of the other elements present.

11. A catalyst having the empirical formula:

$$Mo_aSb_bV_cY_dZ_eO_f$$

wherein
Y can be one or more of the elements selected from the group consisting of silver, magnesium, thallium and cadmium; and
Z can be one or more of the elements of the group consisting of manganese, cobalt, nickel, copper, iron, tin, chromium, titanium, bismuth, rhenium, and zinc; and
wherein the number of atoms of each element present is represented by $a$ through $f$,
wherein
$a$ is a number from 6 to 18;
$b$ is a number from 0.1 to 6;
$c$ is a number from 0.1 to 6;
$d$ is a number from 0.01 to 6;
$e$ is a number from 0 to 6; and $f$ is a number that satisfies the valence requirements of the other elements present.

12. The catalyst in claim 11 wherein Y is silver.
13. The catalyst in claim 11 wherein Y is magnesium.
14. The catalyst in claim 11 wherein Y is thallium.